United States Patent [19]

Küepper et al.

[11] 3,974,231

[45] Aug. 10, 1976

[54] PROCESS FOR THE PRODUCTION OF PURE CYCLOPENTENE

[75] Inventors: Friedrich-Wilhelm Küepper; Roland Streck, both of Marl, Germany

[73] Assignee: Chemische Werke Huls Aktiengesellschaft, Marl, Germany

[22] Filed: Apr. 30, 1974

[21] Appl. No.: 465,515

[30] Foreign Application Priority Data

May 23, 1973 Germany............................ 2326196

[52] U.S. Cl............................................... 260/666 A
[51] Int. Cl.²...................... C07C 3/62; C07C 13/12
[58] Field of Search..................... 260/666 A, 683 D

[56] References Cited
UNITED STATES PATENTS

| | | | |
|---|---|---|---|
| 3,558,518 | 1/1971 | Zuech | 260/666 A |
| 3,634,539 | 1/1972 | Alkema et al. | 260/683 D |
| 3,793,381 | 2/1974 | Kohler et al. | 260/666 A |
| 3,816,384 | 6/1974 | Streck et al. | 260/666 A |

*Primary Examiner*—Veronica O'Keefe
*Attorney, Agent, or Firm*—Millen, Raptes & White

[57] ABSTRACT

A process for the production of cyclopentene free of $C_5$-diene impurities, which comprises metathetically reacting cis-cis-cyclodecadiene-(1,6) with a catalytic amount of a metathesis catalyst at a reaction temperature of from 0°C up to the temperature at which said catalyst decomposes for a period of time sufficient to form said cyclopentene.

11 Claims, No Drawings

PROCESS FOR THE PRODUCTION OF PURE CYCLOPENTENE

BACKGROUND OF THE INVENTION

This invention relates to a process for the production of pure cyclopentene.

It is known to obtain cyclopentene from diolefin-containing hydrocarbon mixtures, e.g., pyrolysis benzines or cracked gasoline, containing cyclopentene, cyclopentadiene and/or dicyclopentadiene by selectively hydrogenating the diolefins in the hydrocarbon mixture to monoolefins and isolating the cyclopentene by distillative separation, e.g., see German Unexamined Laid-Open Application DOS No. 1,643,947.

Furthermore, it is known from DOS No. 1,793,254 to obtain cyclopentene, together with isoprene and a diolefin stream containing essentially 1,3-pentadiene and cyclopentadiene, from $C_5$-hydrocarbon mixtures by subjecting the hydrocarbon mixture to a liquid-liquid extraction with 1-oxo-1-methyl-phospholine as the selective solvent, in combination with an extractive distillation. DOS No. 1,793,256 likewise describes a process for the separation of $C_5$-hydrocarbon mixtures and for obtaining polymerizable cyclopentene, using N-methyloxazolidone as the selective solvent.

It is furthermore known from DOS No. 1,793,273 to separate the selective solvent, after liquid-liquid extraction and extractive distillation, in a liquid-liquid counter extraction from the $C_5$-diolefins with a second solvent and to employ a portion of the $C_5$-hydrocarbon vapors at the head of the distillation column for separation of the second solvent from the diolefins to operate the extractive distillation stage.

DOS No. 2,025,411 describes the production of cyclopentene from cyclopentadiene by partial hydrogenation with molecular hydrogen in the gaseous phase at temperatures of above 50°C with a supported hydrogenation catalyst containing palladium as the active components with additives of chromium and/or titanium.

Finally, it is known from DOS No. 2,131,791 to treat cyclopentene containing olfefinic and diolefinic $C_5$-hydrocarbon impurities with an acidic cation exchanger and thereafter to separate cyclopentene from the thus-obtained product by means of distillation.

All of the above-described processes in the present state of the art presuppose the isolation of cyclopentadienecyclopentene mixtures from $C_5$-cuts, which are commercially available only in limited amounts so that quantitative production of cyclopentene is limited. A further disadvantage of such processes is that economical isolation of the cyclopentene is possible only in conjunction with simultaneous exploitation of the isoprene component of the $C_5$-cut. A usable quality of cyclopentene is obtained only by way of several stages, some of which are technologically complicated. Furthermore, since a complete lack of diene in the cyclopentene, desirable for a polymerization of the cyclopentene with the aid of so-called metathesis catalysts, is not ensured in the prior art processes, there is often an increased comsumption of catalyst consumption polymerization. This, in turn, leads to either more expensive working-up processes or to an increased ash content in the polymers.

OBJECTS OF THE INVENTION

Accordingly, it is a general object of the present invention to provide a process for the production of pure cyclopentene which minimizes or eliminates the above-mentioned problems facing the current state of the art.

Another object of the present invention is to provide a new method for the direct preparation of pure cyclopentene.

A further object of the present inventon is to provide a process for the production of pure cyclopentene which does not employ the conventional $C_5$-hydrocarbon mixtures as a starting material.

An additional object of the present invention is to provide a method for the production of cyclopentene free from contamination with $C_5$-dienes.

Yet another object of the present invention is to eliminate the hydrogenation step heretofore employed in the preparation of cyclopentene.

Other objects and advantages of this invention will become apparent to those skilled in the art upon further study of the specification and appended claims.

SUMMARY OF THE INVENTION

Briefly, the above and other objects are attained in one aspect of the present invention by providing a process for the production of cyclopentene free of $C_5$-diene impurities which comprises metathetically reacting cis-cis-cyclodecadiene-(1,6) with a catalytic amount of a metathesis catalyst, at a reaction temperature of from 0°C up to the temperature at which said catalyst decomposes, for a period of time sufficient to form said cyclopentene.

DETAILED DISCUSSION

It has now been found that pure cyclopentene can be produced in an elegantly simple manner by metathetically reacting cis-cis-cyclodecadiene-(1,6), optionally in the presence of an inert solvent, at temperatures of above 0°C.

The pure cyclopentene produced according to the present invention is a product which inherently does not contain any conjugated dienes which can be confirmed by ultraviolet spectroscopy, e.g., cyclopentadiene, and such a product is especially valuable for subsequent polymerization with the aid of metathesis catalysts.

The starting material employed in the process of this invention, cis-cis-cyclodecadiene-(1,6), can be produced in accordance with known processes. For example, cis-transcyclodecadiene-(1,5) can first be produced from the inexpensive monomers butadiene and ethylene, which are available in almost unlimited amounts, e.g., see G. Wilke and P. Heimbach, "Angew. Chemie" (Applied Chemistry) 75: 10 (1963). This cis-trans-cyclodecadiene-(1,5) can then be converted to cis-cis-cyclodecadiene-(1,6) with the aid of an isomerizing catalyst, e.g., see German Patent No. 1,230,023 or dissertation by H. G. Nuessel, Ruhr University Bochum (1970), p. 89.

As is known, metathesis catalysts are understood to mean homogeneous and heterogeneous catalysts containing compounds of metals of Subgroups V to VII of the Periodic Table, predominantly compounds of niobium, tantalum, molybdenum, tungsten and rhenium, as well as optionally compounds of the metals of main Groups I to III of the Periodic Table, e.g., the alkyls or hydrides thereof, optionally with further ligands, e.g., halogen, alkoxyl, or carboxylate or, in place thereof, Lewis acids. The metathesis catalysts, as is known, can further contain activating additives, e.g., alcohols, epoxides, tert.-butyl hypochlorite, peroxides, carboxylic acids, aromatic nitro compounds, vinyl halides, vinyl and allyl ethers, vinyl and allyl esters, etc.

It is known that cyclic olefins having at least one unsubstituted ring double bond can be polymerized by ring opening employing the so-called metathetical catalysts, e.g., a Ziegler-Natta catalyst system comprising (a) a soluble compound of a metal of Subgroups V through VII of the Periodic Table, and (b) a soluble alkyl or hydride of a metal of Main Groups I through III of the Periodic Table, and optionally catalyst activators, e.g., see U.S. Pat. Nos. 3,458,489; 3,459,725; 3,666,742; 3,476,728; 3,492,245; 3,492,278; 3,502,626; 3,691,253; and German Applications DOS Nos. 1,720,798; 1,770,143; 1,805,158; 1,954,092 and 2,058,198.

As is known, the aforementioned mixed catalysts are capable of polymerizing cyclic olefins having at least one unsubstituted ring double bond, with ring opening, e.g., see German Published Application No. 1,299,868 and German Unexamined Published Application No. 1,570,940. Such mixed catalysts can effect the disproportionation of open-chain olefins, e.g., see German Unexamined Published Application No. 1,618,466.

The same catalysts which promote the ring-opening polymerization of cycloolefins are also known to be effective in the olefin metathesis reactions wherein acyclic internal olefins undergo a structural rearrangement, e.g., 2 $R_1$—CH=CH—$R_2$ $\rightarrow$ $R_1$ CH=CH$R_1$, + $R_2$CH=CH$R_2$ as described, inter alia, by Calderon et al., Tetrahedron Letters 1967: 3327, J. Am. Chem. Soc. 90: 4132 (1968) and in C & E News 45 (41) : 51 ff. (1969).

It is also known from German Patent No. 1,929,140 and German Unexamined Published Application Nos. 2,058,183 and 2,016,471 to use these mixed catalysts in producing copolymers from polyolefinically unsaturated hydrocarbon polymers and either cyclic or acyclic olefinically unsaturated hydrocarbon monomers.

In principle, all metathesis catalysts suitable for the polymerization of cyclic olefins having at least one unsubstituted ring double bond are useful in the process of the present invention. Many such catalysts are well known in the art and include but are not limited to those meeting one or more of the following criteria:

a. those in which component (a) is a transition metal halide;

b. those in which the metal of component (a) is tungsten or molybdenum, especially when component a) is a chloride thereof;

c. those in which component (a) is a tungsten halide, especially tungsten hexachloride;

d. those in which component (b) is an alkyl compound;

e. those in which component (b) is an alkylaluminum halide, especially the chloride, of the formula $AlR_mX_n$ wherein R is lower alkyl of 1–6 carbon atoms, preferably ethyl; X is halogen, preferably chloride; $m$ is a whole or fractional number from 1 to 2 inclusive; $n$ is a whole or fractional number from 1 to 2 inclusive; and the sum of $m + n$ equals 3;

f. those of (a) through (e) inclusive together with an alkanol catalyst modifier.

Presently preferred metathesis catalysts are tungsten hexachloride, ethanol and ethyl aluminum dichloride, preferably with a molar ratio of the individual components of 1:1 – 3:4 – 5, and especially with a molar ratio of ethanol to tungsten hexachloride of 3 : 1.

The reaction can optionally also be accomplished in an inert solvent, i.e., one which does not interfere with metathetical reactions employing the aforementioned catalysts. Suitable inert solvents are well known in the art and are generally characterized as aliphatic, alicyclic, aromatic and/or halogenated hydrocarbons. Suitable such solvents include but are not limited to aliphatic hydrocarbons, e.g., pentane, hexane, heptane, n- and iso-octane, isononane (hydrogenated propene trimer), n-decane, isododecane (hydrogenated propene tetramer); cycloaliphatic hydrocarbons, e.g., cyclopentane, cyclohexane and the substitution products thereof, e.g., methylcyclopentane, methylcyclohexane, ethylcyclohexane, isopropylcyclohexane, cyclooctane, decahydronaphthalene, etc; aromatic hydrocarbons, e.g., benzene, toluene, o-, m-, p-xylene, ethylbenzene, o-, m-, p-diethylbenzene, m-propylbenzene, isopropylbenzene, other mono- to polyalkyl benzenes, tetrahydronaphthalene, etc; and halogenated derivatives of the above, e.g., methylene chloride, chloroform, carbon tetrachloride, 1,2-dichloroethylene, trichloroethylene, tetrachloroethylene, chlorobenzene, o-dichlorobenzene, trichlorobenzene (mixture of isomers), bromobenzene, fluorobenzene, 1,2-dichloroethane, etc.

Preferably, solvents are employed which cannot participate as reactants in a Friedel-Crafts reaction with olefins present, i.e. the starting material or the cyclopentene product, so as to avoid Friedel-Crafts side reactions.

It is essential that the inert solvents be made maximally free of water and other proton donors, as well as of compounds having electron donor functions (Lewis bases), by means of a suitable known purification technique. Except for very small quantities which are optionally used for obtaining special effects, such impurities generally impair the catalyst activity.

The process of the present invention is generally conducted at temperatures of above 0°C. The reaction temperature has an upper limit determined by the thermal stability of the catalyst and a lower limit determined by an excessive reduction of the reaction velocity. The process is advantageously carried out at temperatures of between 40° and 180°C, especially between 70° and 120°C. Reaction times required are those typical of metathesis reactions and vary from several minutes to several days, generally 0.5 –5 hours at the preferred temperatures.

After a satisfactory conversion has been attained, as determined by, e.g., gas chromatography the catalyst is inactivated and/or separated, and the thusproduced separated, is isolated by distillation. The unreacted cis-cis-cyclodecadiene-(1,6) can be recycled into the reaction process after having been worked up appropriately, e.g., by fractional distillation and/or recrystallization.

The cyclopentene product produced according to the process of the present invention is completely free of $C_5$-diolefins so long as there are no diolefin contaminants in either the cis-cis-cyclodecadiene-(1,6) starting material or the solvent employed except, of course, for unreacted starting material which is readily separated from the cyclopentene product, e.g., by simple distillation. As both the starting material and solvent are readily obtainable or easily purified to be free of diolefin contaminants and as none are inherently produced in the course of the reaction, unreacted starting material can be readily recycled. Thus, the process can be conducted batchwise, discontinuously or continuously resulting in substantial savings in both materials and steps employed. Furthermore, since usable yields are obtained under mild reaction conditions in relatively brief reaction times, the process itself is particularly economical. Thus, it will generally but not always be advantageous to terminate the reaction after a yield of 10-15 % has been reacted, based on conversion of the starting material, although higher yields, e.g., of 20-30 % or even higher, can be obtained if desired.

The cyclopentene produced according to the process of this invention is excellently suited for use in the production of trans-1,5-polypentenamer rubber which is of great technical interest, e.g., see Hydrocarbon Processing, December 1972, p. 71. The preparation of cyclopentene according to the present process is surprising insofar as cis-cis-cyclodecadiene-(1,6) cannot be converted into unsaturated high molecular weight products by means of the metathesis catalysts described herein within the temperature range which is utilized for the preparation of polyalkenamers from other cycloolefins, and would thus appear to be unsuitable for the metathesis reaction. On the contrary, attempts to polymerise cis-cis -cyclodecadiene-(1,6) with a combination of $WCl_6/C_2H_5OH/C_2H_5AlCl_2$ under the conditions suitable for the polymerisation of cyclopentene (−30° to 0°C) led to almost completely saturated low molecular weight products instead of the expected high molecular weight polypentenamers. From these results the conclusion seems evident to anybody skilled in the art that cis-cis-cyclodecadiene-(1,6) does not participate in metathesis reactions.

While not wishing to be bound by any theory of the invention, it is believed that the metathesis reaction of the present invention takes place as follows:

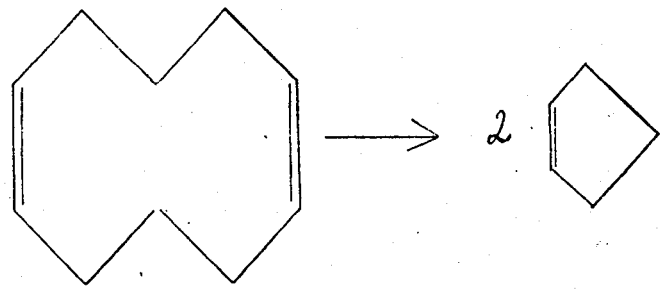

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLES 1–6

Five grams of cis-cis-cyclodecadiene-(1,6) was mixed, in a so-called Schlenk-vessel under an inert atmosphere (argon or nitrogen) with a catalyst having the following composition : 0.1 millimole of $WCl_6$ (0.05-molar solution in benzene), 0.3 mmole of ethanol (1-molar solution in cyclohexane) and 0.5 mmole of ethyl aluminum dichloride (1-molar solution in cyclohexane). Thereafter, the mixture was heated in the sealed apparatus to the desired reaction temperature under agitation. Samples were withdrawn after various reaction times, yielding the following results by gas chromatography analysis ("Carbowax" 20 M on "Embacel" and/or ethylene glycol bis(2-cyanoethylether) on Embacel were utilized as the column filling):

| Example No. | Reaction Temperature (°C) | Reaction Time (min.) | Cyclopentene, As % of cis-cis-cyclodecadiene-(1,6) Charged | % $C_5$ Dienes |
| --- | --- | --- | --- | --- |
| 1 | 50 | 45 | 4.9 | 0.0 |
| 2 | 50 | 135 | 5.6 | 0.0 |
| 3 | 50 | 315 | 5.9 | 0.0 |
| 4 | 80 | 45 | 15.8 | 0.0 |
| 5 | 80 | 135 | 19.8 | 0.0 |
| 6 | 80 | 315 | 20.5 | 0.0 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

By the term "free of $C_5$-diene impurities" as used herein is meant a $C_5$-diene content of less than 0.1 wt. %, preferably less than 0.05 wt. % based on the total reaction mixture.

What is claimed is:

1. A process for the production of cyclopentene free of $C_5$-diene impurities, which comprises metathetically reacting a reaction mixture consisting essentially of cis,ciscyclodecadiene-(1,6) with a catalytic amount of a metathesis catalyst capable of promoting the ring-opening polymerization of cyclic olefins having at least one unsubstituted ring double bond which metathesis catalyst is a Ziegler-Natta catalyst consisting essentially of (a) a solvent soluble component of tungsten or molybdenum and (b) a solvent soluble alkylaluminum halide of the formula $AlR_mX_n$ wherein R is lower alkyl of 1-6 carbon atoms, X is halogen, $m$ is a whole or fractional number from 1 to 2 inclusive and the sum of $m + n$ equals 3, at a metathesis reaction temperature of from 0° C. up to the temperature at which said catalyst decomposes for a period of time sufficient to form a reaction product consisting essentially of cyclopentene having a $C_5$-diene content of less than 0.1 weight percent of the total reaction mixture.

2. A process according to claim 1, wherein the reaction temperature is 40°–180° C.

3. A process according to claim 1, wherein the catalyst further comprises a metathesis activating amount of an alkanol.

4. A process according to claim 1, wherein component (a) is a tungsten chloride or a molybdenum chloride.

5. A process according to claim 4, wherein R is ethyl and X is chloride.

6. A process according to claim 5, wherein the molar ratio of (a) : (b) is about 1 : 4–5.

7. A process according to claim 6, wherein component (a) is tungsten hexachloride and component (b) is ethylaluminum dichloride.

8. A process according to claim 7, wherein the catalyst further comprises a metathesis activating amount of ethanol.

9. A process according to claim 8, wherein the molar ratio of ethanol to tungsten hexachloride is about 1–3 : 1.

10. A process according to claim 9, wherein the reaction temperature is 70°–120° C.

11. A process according to claim 1, wherein the reaction is effected in a inert diluent selected from the group consisting of aliphatic, alicyclic, aromatic and/or halogenated hydrocarbons which cannot participate in a Friedel-Crafts reaction with olefins present.

* * * * *

UNITED STATES PATENT AND TRADEMARK OFFICE
CERTIFICATE OF CORRECTION

PATENT NO. : 3,974,231
DATED : August 10, 1976
INVENTOR(S) : Küpper et al.

It is certified that error appears in the above-identified patent and that said Letters Patent are hereby corrected as shown below:

The inventor's name should read --Küpper--et al.

Column 6, line 54, change "component" to --compound--.

Signed and Sealed this

Sixteenth Day of November 1976

[SEAL]

Attest:

RUTH C. MASON
*Attesting Officer*

C. MARSHALL DANN
*Commissioner of Patents and Trademarks*